United States Patent [19]

Bush

[11] Patent Number: 5,456,904

[45] Date of Patent: Oct. 10, 1995

[54] PHOTOPROTECTION COMPOSITIONS COMPRISING CERTAIN CHELATING AGENTS

[75] Inventor: Rodney D. Bush, Fairfield, Ohio

[73] Assignee: The Procter & Gamble Company, Cincinnati, Ohio

[21] Appl. No.: 83,418

[22] Filed: Jun. 28, 1993

[51] Int. Cl.$^6$ .................................................. A61K 7/42
[52] U.S. Cl. .................................................. 424/59; 424/60
[58] Field of Search .......................................... 424/59, 60

[56] References Cited

U.S. PATENT DOCUMENTS

| | | | |
|---|---|---|---|
| 3,728,461 | 4/1973 | Dourus et al. | 424/251 |
| 3,920,808 | 11/1975 | Fusaro | 424/59 |
| 3,928,017 | 12/1975 | Duoros, Jr. et al. | 71/67 |
| 3,951,840 | 4/1976 | Fujino et al. | 252/102 |
| 4,145,413 | 3/1979 | Vsdin et al. | 424/63 |
| 4,595,591 | 6/1986 | Mardi et al. | 424/127 |
| 4,842,868 | 6/1989 | Helwing | 424/486 |
| 5,100,658 | 3/1992 | Bolich et al. | 424/70 |
| 5,104,646 | 4/1992 | Bolich et al. | 424/70 |
| 5,106,609 | 4/1992 | Bolich et al. | 424/70 |
| 5,118,707 | 6/1992 | Chatterjee et al. | 514/469 |
| 5,238,965 | 8/1993 | Piazza et al. | 514/844 |
| 5,296,500 | 3/1994 | Hillebrand | 514/562 |

OTHER PUBLICATIONS

Chemical Abstracts 94:128408x (1981).
Burbello, "Protective Effect of Antioxidants in Methemoglobinemia Induced by Sodium Nitrite Under Experimental Conditions", *STN International, Karlsruhe File Chem. Abstracts*, vol. 8, pp. 13–15, (1991).
Awadallah, "Synthesis and Biocidal Activity Studies on Solid Complexes of Iron (II,II), Cobalt(II,III) and Nickel(II) with Violuric Acid and Dinitroresorcinol", *J. Indian Chem. Soc.*, vol. 65, No. 8, pp. 532–534, (1988).
Vandewalle, "Contribution a L'etude Des Composes Nitroses de la Pyrimidine; V. Complexes Mixtes de l'ion Fereux.", *Bull. Soc. Chim. Fr.*, No. 5–6, pp. 209–212, (1981).
Vandewalle, "Contribution a Letude des Proprietes Complexantes de l'acide Monomethylviolurique", *C. R. Hebd. Seances Acad. Sci., Ser. C.*, vol. 284, No. 13, pp. 491–494, (1977).
Lagercrantz, C., "Trapping of Hydrogen Atoms Formed in the Photochemical Reaction Involving Hydrogen Peroxide, Methanol or Dimethyl Sulfoxide by Addition to α–Nitroso–β–hydroxy Compounds", *Acta Chem. Scand.* vol. 43 (Nov. 1989) pp. 509–510.
Leermakers, P. A., et al., "Chelates of Violuric Acid", *J. Chem. Soc.*, vol. 80 (Nov. 1958) pp. 5663–5667.
Moratal, J., et al., "Violurato Complexes of Fe(II), Co(II) and Cu(II) in DMSO Solution. A Potentiometric Study", *Revue de Chimie Minérale*, vol. 19 (1982) pp. 72–79.
Moratal, J., et al., "Calorimetric and Potentiometric Study of the Deprotonation Reactions of Violuric Acids," *Thermochimica Acta*, vol. 89 (1985) pp. 343–350.
Raimova, N. V., et al., "Light Absorption of Violuric Acid in Solutions", *Chem. Abstracts*, vol. 79 (1973) pp. 330–331, Abstract No. 151260s.
Raimova, N. V., et al., "Light Absorption of Violuric Acid in Solutions", *Izv. Vyssh. Icheb. Zaved., Khim. Khim. Tekhnol.* vol. 16, No. 8 (1973) pp. 1223–1226. (no translation).
Vandewalle, Y., "Préparation, Acidités et Propriétés Complexantes de L'acide Monoéthyliolurique", *C. R. Acad. Sc. Paris*, vol. 289 (Oct. 1979) pp. 215–217.
Vandewalle, Y., et al., "Étude de L'acide 1.3 Diméthyliolurique:Préparation, Acidité et Propriétés Complexantes", *C.R. Acad. Sc. Paris*, vol. 282 (Jun. 1986) pp. 1073–1076. (plus translation).

*Primary Examiner*—Shep Rose
*Attorney, Agent, or Firm*—Richard A. Hake; John M. Howell; David L. Suter

[57] ABSTRACT

The subject invention relates to methods and compositions comprising: a) from about 0.1% to about 5% of a compound having the structure selected from the group consisting of:

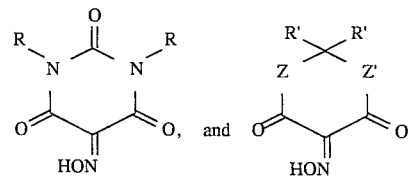

wherein each R is independently selected from the group consisting of hydrogen, alkyl, and aryl; each R' is independently selected from the group consisting of hydrogen, alkoxy, and alkyl; Z and Z' are independently selected from the group consisting of NH, O, and $CH_2$ such that when Z or Z' is NH, the other is not O; or a pharmaceutically acceptable salt of any of the aforementioned compounds; and b) a pharmaceutically-acceptable topical carrier.

12 Claims, No Drawings

PHOTOPROTECTION COMPOSITIONS COMPRISING CERTAIN CHELATING AGENTS

TECHNICAL FIELD

This invention relates to topical compositions useful for protecting the skin from the harmful effects of ultraviolet irradiation, such as sunburn and sun-induced premature aging of the skin.

BACKGROUND OF THE INVENTION

The damaging effects of sunlight on skin are well documented. Much damage is due to routine day-to-day activities in the sunlight.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983. Hence, although the immediate effects of ultraviolet radiation may be cosmetically and socially gratifying, the long-term hazards are cumulative and potentially serious. include titanium dioxide and zinc oxide. However, these agents are very susceptible to rub-off or wear-off, resulting in little or no protection.

The most common agents for sun protection are sunscreens. These agents exert their effects through absorption of ultraviolet radiation so that it cannot penetrate the skin. Sunscreens must remain on the surface of the skin during exposure. However, sunscreens are easily rubbed off or washed off by sweating or swimming and can also be lost by penetration into the skin.

It is well-known that ultraviolet light induces inflammation of the skin and harmful photochemical reactions therein. During exposure and as repair of the UV damage takes place, super-oxide ($O_2^-$) radicals are formed in the skin. UV iradiation also causes some microvascular damage in the skin. This leads to local hemorrhage and "leakage" of blood cells into the dermis. Iron from the hemoglobin accumulates in the extra-cellular matrix of the tissue as $Fe^{+2}$ and $Fe^{+3}$. It is known that iron catalytically participates in the conversion of superoxide radicals to hydroxyl radicals, a species which is known to be very damaging to tissue.

It is an object of the subject invention to provide a topical composition, the use of which will prevent chronic (photoaging) effects of exposure to the sun.

It is also an object of the subject invention to provide a topical composition, the use of which will prevent acute (erythema) effects of exposure to the sun.

It is also an object of the subject invention to provide a topical composition for preventing the deleterious effects of the sun with minimal interference to the tanning response.

It is further an object of the subject invention to provide a photoprotective composition which penetrates into the skin and which has low susceptiblility to rub-off, wear-off or wash-off.

It is a still further object of the subject invention to provide a photoprotective composition which can be applied to the skin in advance of UV exposure without significant loss of efficacy.

It is also an object of the subject invention to provide a method for preventing the deleterious effects of the sun with minimal interference to the tanning response.

SUMMARY OF THE INVENTION

The subject invention relates to compositions comprising: A) from about 0.1% to about 5% of a compound having a structure selected from the group consisting of:

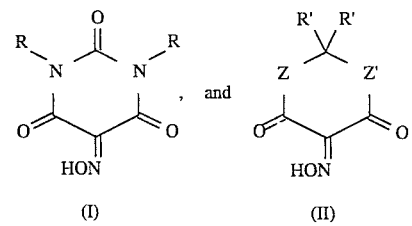

wherein each R is independently selected from the group consisting of hydrogen, alkyl, and aryl; each R' is independently selected from the group consisting of hydrogen, alkoxy, and alkyl; Z and Z' are independently selected from the group consisting of NH, O, and $CH_2$ such that when Z or Z' is NH, the other is not O; or a pharmaceutically acceptable salt of any of the aforementioned compounds; and B) a pharmaceutically-acceptable topical carrier.

DETAILED DISCLOSURE OF THE INVENTION

As used herein, "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indicated hereinbelow, alkyl are preferably as follows: preferred alkyl are straight or branched chain, more preferably branched chain. Preferred alkyl are mono-, di-, or trisubstituted, or unsubstituted, more preferably monosubstituted or unsubstituted. Preferred alkyl are saturated or unsaturated, preferably saturated; if unsaturated, preferably there is from one to three unsaturations; more preferably, one or two unsaturations; still more preferably, one unsaturation. Preferred alkyl are $C_1$–$C_{18}$ alkyl; more preferred are $C_1$–$C_{10}$ alkyl; still more preferred are $C_1$–$C_4$ and $C_4$–$C_6$ alkyl.

3

As used herein, "alkoxy" means an —O—alkyl moiety.

As used herein, "carboxy" and "carboxy acid" mean a —COOH moiety. "Carboxy ester", as used herein, means a —COO—alkyl moiety.

As used herein, "aryl" means substituted or unsubstituted phenyl. Preferred substituents include alkyl, halogen, and hydroxy.

As used herein, "substituted", in reference to alkyl groups, means such groups that can be mono- or polysubstituted. As used in this paragraph, "R" refers to an alkyl group. Preferred substituents are selected from halogen, hydroxy, alkoxy, carboxy, carboxy esters, oxo, thiol, alkylthio (R—S—), alkyldithio (R—S—S—), amino, alkylamino, dialkylamino, amide, alkylamide, dialkylamide, and alkylsilyl (R—Si) $(CH_3)_2$.

As used herein, "safe and photoprotectively effective amount" means an amount sufficient to substantially reduce the deleterious effects of ultraviolet radiation to skin but not so much as to cause serious side effects or adverse skin reactions.

As used herein, "regulating" means preventing, retarding, or arresting.

As used herein, all percentages are by weight unless otherwise specified.

The subject invention involves compounds, referred to herein as "active compounds", having a structure selected from the group consisting of:

(I)                (II)

wherein each R is independently selected from the group consisting of hydrogen, alkyl, and aryl; each R' is independently selected from the group consisting of hydrogen, alkoxy, and alkyl; Z and Z' are independently selected from the group consisting of NH, O, and $CH_2$ such that when Z or Z' is NH, the other is not O; or a pharmaceutically acceptable salt of any of the aforementioned compounds.

Preferred active compounds are comprised of a total of about 26 atoms or fewer, excluding hydrogen, and have a molecular weight of less than one thousand. Heavier and larger active compounds generally will not penetrate the skin as well as is necessary for good efficacy.

Preferred is both R being the same. Preferred R are hydrogen or alkyl.

If R is alkyl, preferred alkyl are $C_1$–$C_{18}$ alkyl; also preferred are $C_2$–$C_{10}$ alkyl; also preferred are $C_3$–$C_8$ alkyl; more preferred are $C_1$–$C_4$ and $C_4$–$C_6$ alkyl. Preferred alkyl are branched or straight chain, more preferably branched; more preferred is branched wherever feasible, to render the molecule more compact. The alkyl may be saturated or unsaturated, preferably saturated; if unsaturated, triple bonds are preferable to double bonds. If unsaturated, preferably there is from one to three unsaturations; more preferably, one or two unsaturations; still more preferably, one unsaturation. Preferred alkyl may be substituted or unsubstituted, preferably substituted. If substituted, preferably there are from 1 to about 5 substituents; more preferably, from about 1 to about 3 substituents, more preferably still,

4 from about 1 to about 2 substituents. Preferred alkyl R include $C_3$–$C_6$ branched chain alkyl, $C_1$–$C_6$ straight chain substituted alkyl, and $C_1$–$C_4$ straight chain unsubstituted alkyl. Also preferred alkyl R are methyl or ethyl.

If R is substituted alkyl, preferred substitutuents are alkoxy, oxo, carboxy, carboxy ester, amino, alkylamino, dialkylamino, amide, alkylamide, dialkylamide; more preferred substituents are selected from alkoxy, oxo, carboxy ester, amino, alkylamino, and dialkylamino. More preferably still, substituted alkyl R are selected from ethoxyethyl (—$CH_2CH_2OCH_2CH_3$), carbethoxymethyl (—$CH_2COOCH_2CH_3$), and hydroxymethyl (—$CH_2OH$).

If R is cyclic alkyl, preferably it is selected from the group consisting of unsubstituted cyclopropyl, unsubstituted cyclopentyl, and unsubstituted cyclohexyl.

If R is aryl, it may be unsubstituted or substituted phenyl. Preferred substituents include alkyl, halogen, and hydroxy. Preferred substituents include $C_1$–$C_4$ alkyl, more preferred are $C_1$–$C_2$ unsubstituted alkyl. Preferred aryl R is unsubstituted phenyl.

If R contains a halogen substituent, preferably the substituent is is iodine; more preferably bromine; more preferably still, chlorine; still more preferably, it is fluorine.

Preferred is both Z and Z' being the same. Preferably Z and Z' are O or $CH_2$; more preferably Z and Z' are O.

Preferred is both R' being the same. Preferred R' are alkyl.

If R' is alkyl, preferred alkyl are $C_1$–$C_{18}$ alkyl; more preferred are $C_2$–$C_{10}$ alkyl; still more preferred are $C_3$–$C_8$ alkyl; still more preferred are $C_4$–$C_6$ alkyl. The alkyl are branched or straight chain, more preferably branched; more preferred is branched wherever feasible, to render the molecule more compact. The alkyl may be saturated or unsaturated, preferably saturated; if unsaturated, triple bonds are preferable to double bonds. If unsaturated, preferably there is from one to three unsaturations; more preferably, one or two unsaturations; still more preferably, one unsaturation. Preferred alkyl may be sustituted or unsubstituted, preferably substituted. If substituted, preferably there are from 1 to about 5 substituents, more preferably from about 1 to about 3 substituents, more preferably still from about 1 to about 2 substituents. Preferred alkyl R' include $C_3$–$C_6$ branched chain alkyl, $C_1$–$C_6$ straight chain substituted alkyl, and $C_1$–$C_4$ straight chain unsubstituted alkyl. Also preferred alkyl R' are methyl or ethyl. If R' is substituted alkyl, preferred substitutuents include alkoxy, oxo, carboxy, carboxy ester and halogen. Preferred substitutuents are selected from alkoxy, and fluoro. More preferably, substituted alkyl R' are selected from ethoxyethyl (—$CH_2CH_2OCH_2CH_3$), fluoromethyl (—$CH_2F$), difluoromethyl (—$CHF_2$), and trifluoromethyl (—$CF_3$).

If R' contains a halogen substituent, preferably the substituent is iodine; more preferably bromine; more preferably still, chlorine; still more preferably, it is fluorine.

If R' is cyclic alkyl, preferably it is selected from unsubstituted cyclopropyl, cyclohexyl, and cyclopentyl.

If R' is alkoxy, preferably the alkyl moiety of the alkoxy is $C_1$–$C_{10}$ alkyl, more preferably, $C_2$–$C_8$ alkyl, more preferably still, $C_4$–$C_6$ alkyl.

Preferred active compounds of the subject invention include:

violuric acid, 1,3-di(ethoxyethyl)-violuric acid:

-continued 1,3-di(carbethoxymethyl)-violuric acid:

$CH_3CH_2OCH_2CH_2\underset{N}{}\overset{\overset{O}{\|}}{\underset{}{C}}\underset{N}{}CH_2CH_2OCH_2CH_3$, with ring completed by two C=O groups and =NOH 1,3-di(hydroxymethyl)-violuric acid:

$CH_3CH_2OCCH_2\underset{N}{}\overset{\overset{O}{\|}}{\underset{}{C}}\underset{N}{}CH_2COCH_2CH_3$, with =NOH 1,3-di(n-butyl)-violuric acid:

$HOH_2C\underset{N}{}\overset{\overset{O}{\|}}{\underset{}{C}}\underset{N}{}CH_2OH$, with =NOH 1,3-diethyl-violuric acid:

$CH_3CH_2CH_2CH_2\underset{N}{}\overset{\overset{O}{\|}}{\underset{}{C}}\underset{N}{}CH_2CH_2CH_2CH_3$, with =NOH 2,2-dimethyl-1,3-dioxane-4,6-dione-5-oxime:

$CH_3CH_2\underset{N}{}\overset{\overset{O}{\|}}{\underset{}{C}}\underset{N}{}CH_2CH_3$, with =NOH 5,5-dimethyl-1,3-cyclohexanedione-2-oxime:

The active compounds useful in the subject invention are generally moderate UV-light absorbers, but provide surprisingly high values in an SPF test (based on the Test Method hereinbelow). The active compounds are also good metal chelators and provide protection against chronic skin aging and wrinkling due to metal catalyzed free radical formation, which may be caused by skin exposure to UV-light or other causes. Therefore, the compositions of the subject invention which comprise the active compounds can provide excellent protection against both short term (acute) and long term (chronic) exposure to UV-light and against damage due to other causes of metal-catalyzed free radical formation.

Active compounds useful in the subject invention also include metal complexes of the compounds of the subject invention. The active compounds of the subject invention are metal chelators and readily form complexes with metal ions. The inclusion of metal complexed active compounds in the compositions of the subject invention can enhance the acute photoprotection provided by the composition. A metal ion generally complexes with from about 1 to about 3 molecules of an active compound of the subject invention. If metal complexed active compounds are used, preferably each mole of metal ion is "substantially complexed," i.e., is complexed with a number of moles of active compound molecules equal to the metal ion's valence number plus or minus one, more preferably each mole of metal ion is "fully complexed," i.e., is complexed with a number of moles of active compound molecules equal to the metal ion's valence number.

Preferred metal ions for inclusion in the metal complexed active compounds useful in the subject invention include sodium, aluminum, zinc, lithium, magnesium, potassium, calcium, rubidium, strontium, titanium, zirconium, vanadium, chromium, manganese, cobalt, nickel, copper, gallium, scandium, silicon, boron, praseodymium, lanthanum, promethium, samarium, and europium; more preferred metal ions are those which do not have d-electrons: sodium, aluminum, zinc, lithium, magnesium, potassium, calcium and scandium; most preferred metal ions are sodium, aluminum, zinc, lithium, gallium and scandium.

The following non-limiting examples exemplify the synthesis of active compounds useful in the subject invention.

EXAMPLE 1

Violuric acid monohydrate is obtained from Aldrich Chemical Co., 1001 West Saint Paul Avenue, Milwaukee, Wis. 53233.

EXAMPLE 2

1,3-Dimethyl-violuric acid is synthesized as follows: In a 3-liter round-bottomed flask, 35 g of sodium is allowed to react with 500 mL of absolute ethanol under reflux. One hundred eighty grams of ethyl malonate and 85 g of dry dimethylurea (dissolved in 500 mL of absolute ethanol) are then added and the mixture refluxed for 12 hours. At the completion of the reaction, 800 mL of hot water and 90 mL of conc. hydrochloric acid are added with stirring. The mixture is filtered and the filtrate placed in a refrigerator overnight. The result is a white solid, dimethylbarbituric acid.

All of this solid, is placed in a 1-liter flask with 50 mL of concentrated hydrochloric acid, heated and stirred until dissolved. Twenty grams of sodium nitrite as a 10% solution is added with stirring (violent evolution of gas). Pale-pink needles of 1,3-dimethylvioluric acid precipitate and are recrystallized from ethanol. m.p. 139°–140°.

EXAMPLE 3

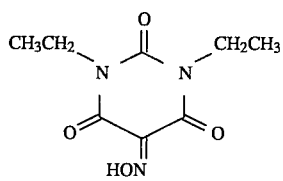

1,3-Diethylvioluric acid is synthesized as follows: In a 3-liter round-bottomed flask, 35 g of sodium is allowed to react with 500 mL of absolute ethanol under reflux. One hundred eighty grams of ethyl malonate and 116 g of dry diethylurea (dissolved in 500 mL of absolute ethanol) are then added and the mixture refluxed for 12 hours. At the completion of the reaction, 800 mL of hot water and 90 mL of conc. hydrochloric acid are added with stirring. The mixture is filtered and the filtrate placed in a refrigerator overnight. The result is diethylbarbituric acid, a white solid.

This solid, is placed in a 1-liter flask with 50 mL of concentrated hydrochloric acid, heated and stirred until dissolved. Twenty grams of sodium nitrite as a 10% solution is added with stirring (violent evolution of gas). Pale-pink needles of 1,3-diethylvioluric acid precipitate and are recrystallized from ethanol.

EXAMPLE 4

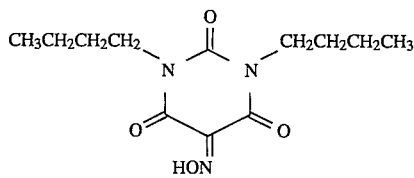

1,3-Di(n-butyl)violuric acid is synthesized as follows: In a 3-liter round-bottomed flask, 35 g of sodium is allowed to react with 500 mL of absolute ethanol under reflux. One hundred eighty grams of ethyl malonate and 172 g of dry dibutylurea (dissolved in 500 mL of absolute ethanol) are then added and the mixture refluxed for 12 hours. At the completion of the reaction, 800 mL of hot water and 90 mL of conc. hydrochloric acid are added with stirring. The mixture is filtered and the filtrate placed in a refrigerator overnight.

The resulting dibutylbarbituric acid is placed in a 1-liter flask with 50 mL of concentrated hydrochloric acid, heated and stirred until dissolved. Twenty grams of sodium nitrite in 10% solution is added with stirring (violent evolution of gas); 1,3-di(n-butyl)violuric acid results.

EXAMPLE 5

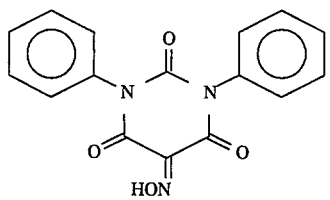

1,3-Diphenylvioluric acid is synthesized by the following procedure. In a 3-liter round-bottomed flask, 35 g of sodium is allowed to react with 500 mL of absolute ethanol under reflux. One hundred eighty grams of ethyl malonate and 202 g of dry diphenylurea (dissolved in 500 mL of absolute ethanol) are then added and the mixture refluxed for 12 hours. At the completion of the reaction, 800 mL of hot water and 90 mL of conc. hydrochloric acid are added with stirring. The mixture is filtered and the filtrate placed in a refrigerator overnight.

The resulting diphenylbarbituric acid is placed in a 1-liter flask with 50 mL of concentrated hydrochloric acid, heated and stirred until dissolved. Twenty grams of sodium nitrite as a 10% solution is added with stirring (violent evolution of gas); 1,3-diphenylvioluric acid, results.

EXAMPLE 6

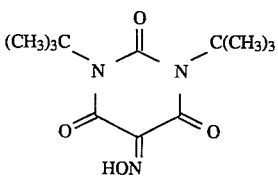

1,3-Di-tert-butylvioluric acid is synthesized by the following procedure. In a 3-liter round-bottomed flask, 35 g of sodium is allowed to react with 500 mL of absolute ethanol under reflux. One hundred eighty grams of ethyl malonate and 172 g of dry di-tert-butylurea (dissolved in 500 mL of absolute ethanol) are then added and the mixture refluxed for 12 hours. At the completion of the reaction, 800 mL of hot water and 90 mL of conc. hydrochloric acid are added with stirring. The mixture is filtered and the filtrate is placed in a refrigerator overnight.

The resulting solid, di-tert-butylbarbituric acid, is placed in a 1-liter flask with 50 mL of concentrated hydrochloric acid, heated and stirred until dissolved. Twenty grams of sodium nitrite as a 10% solution is added with stirring (violent evolution of gas). 1,3-di-tert-butylvioluric acid results and is purified as desired.

EXAMPLE 7

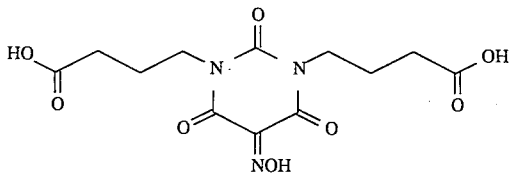

1,3-Di(carboxypropyl)violuric acid is synthesized by the following procedure: 4-Aminobutyaldehyde diethylacetal from Aldrich Chemical is reacted with phosgene in the presence of excess triethylamine to give the corresponding urea. This urea after purification is then place in a flask with ethyl malonate and sodium ethoxide in absolute ethanol and refluxed for 12 hrs. The volatiles are removed by rotoevaporation and the residue extracted with ether. The ether extract is then evaporated to give crude 1,3-di(butane 4',4'-diethylacetal)barbituric acid. This is further purified by preparative HPLC. This material is then reacted with sodium nitrite as in previous examples, followed by a water wash to give the desired 1,3-di(carboxypropyl)violuric acid.

EXAMPLE 8

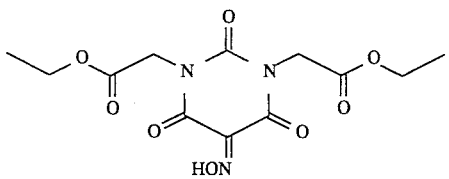

1,3-Di(carbethoxymethyl)violuric acid is synthesized by the following procedure: One equivalent of phosgene is mixed with two equivalents of ethyl glycine and two equivalents of triethylamine in methylene chloride. The resulting precipitate is filtered and the supernate washed and evaporated to give the desired urea. This urea is then added to one equivalent of malonic acid and one equivalent of dicyclohexylcarbodiimide in diethyl ether. The resulting precipitate is filtered and the supernate washed and the volatiles removed. This provides the desired barbituric acid. The acid is then treated with tert-butylnitrite in methylene chloride to give the desired 1,3-di(carbethoxymethyl)violuric acid.

EXAMPLE 9

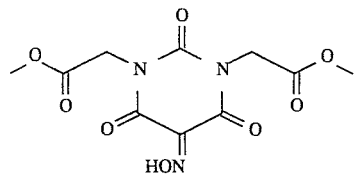

1,3-Di(carbmethoxymethyl)violuric acid is synthesized by following the instructions for the previous example and using methyl glycine in lieu of ethyl glycine.

EXAMPLE 10

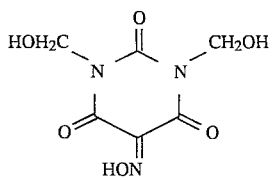

1,3-Di(hydroxymethyl)violuric acid is synthesized by the following procedure: One equivalent of phosgene is mixed with two equivalents of formaldehyde and two equivalents of sodium ethoxide in ethanol. The resulting precipitate is filtered and the supernate washed and evaporated to give the desired urea. This urea is then added to one equivalent of malonic acid and one equivalent of dicyclohexylcarbodiimide in diethyl ether. The resulting precipitate is filtered and the supernate washed and the volatiles removed. This provides the desired barbituric acid. The acid is then treated with tert-butylnitrite in methylene chloride to give the desired 1,3-di(hydroxymethyl)violuric acid, which is purified as desired.

EXAMPLE 11

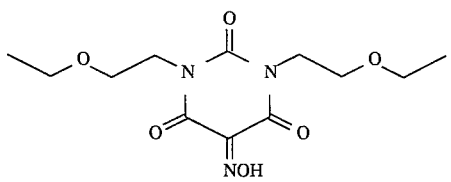

1,3-Di(ethoxyethyl)violuric acid is synthesized as follows: 1-amino-2-ethoxyethane is reacted with phosgene in the presence of excess triethylamine to give the corresponding urea. This urea after purification is placed in a flask with malonic acid and dicyclohexylcarbodiimide and heated in dibutylether. The resulting precipitate is filter off and the volatiles of the supernate is removed by rotoevaporation and the residue extracted with ether. The ether extract is then evaporated to give crude 1,3-di(ethoxyethyl)barbituric acid. This material is then reacted with sodium nitrite as in previous examples followed by a water work up to give the desired product.

EXAMPLE 12

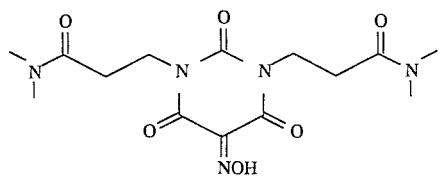

1,3-Di(1-dimethylamino-1-propanoyl)violuric acid is synthesized as follows: 3-Bromopropronic acid (from Aldrich Chemical Company) is dissolved in methylene chloride and treated with one equivalent of thionyl chloride to make the corresponding acid chloride which is then treated with triethyl amine and dimethylamine to provide the corresponding amide. This material is treated with one equivalent of potassium phthalimide to form N,N-dimethyl-3-aminoproprioamide. Two equivalents of this compound are treated with with one equivalent of phosgene to give the urea which is then treated with malonic acid and dicyclohexylcarbodiimide. This barbituric acid is then treated with butylnitrite to give the desired 1,3-di(1-dimethylamino-1-propanoyl)-violuric acid.

EXAMPLE 13

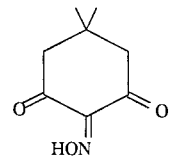

5,5-Dimethyl-1,3-cyclohexanedione 2-oxime is synthesized as follows: 5,5-dimethyl-1,3-cyclohexanedione (20 g, from Aldrich Chem. Co.) is placed in a solution of 10 g of potassium hydroxide in 60 mL of water, then 15 g of potassium nitrite is added while the reaction mixture is cooled in an ice bath. Then 18% hydrochloric acid is added until the solution turns deep blue which then turns reddish-violet and a yellow precipitate is formed. Dilute hydrochloric acid is then added until the solution is such that it produces a stain when tested on starch/potassium iodine paper. The yellow solid is filtered off and recrystalized from water to give 5,5-dimethyl-1,3-cyclohexanedione 2-oxime.

EXAMPLE 14

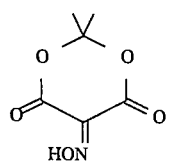

2,2-Dimethyl-1,3-dioxane-4,6-dione 5-oxime is synthesized as follows: 2,2-dimethyl-1,3-dioxane-4,6-dione (14.4g, from Aldrich Chem. Co.) is placed into a 250 mL rounded bottom flask and heated with 12.3 g of butyl nitrite (from Aldrich Chem. Co.) after anhydrous hydrochloric acid is bubbled through the mixture dissolved in 100 mL of chloroform. The resulting product is isolated.

One aspect of the subject invention is pharmaceutical compositions comprising the above compounds. Compositions of the subject invention comprise a safe and effective amount of an active compound useful in the subject invention disclosed hereinabove, preferably from about 0.01% to about 5%, more preferably from about 0.01% to about 2%, still more preferably from about 0.1% to about 1.5%, more preferably still from about 0.5% to about 1%.

At the above preferred concentrations, the ability of the active compounds to act as sunscreens by absorbing ultraviolet light is poor due to the low concentration of the active compounds. in addition, the subject compositions are preferably formulated such that the active compounds penetrate into the skin; this provides optimum photoprotection for the compositions. In contrast, sunscreen compounds provide optimum photoprotection when they remain on the skin surface and do not penetrate the skin. Skin penetration by the subject active compounds is achieved by preferably formulating compositions with active compounds having molecular weight preferably below 1000, more preferably below 500; by preferably formulating compositions with active compounds having a neutral charge in the composition; and by preferably formulating compositions with ingredients which enhance skin penetration of the active compounds.

In addition to the active compound, the compositions of the subject invention comprise a topical pharmaceutically-acceptable carrier. The term "pharmaceutically-acceptable carrier", as used herein, means one or more compatible solid or liquid filler diluents or encapsulating substances which are suitable for administration to a human or lower animal. Such carriers must be of sufficiently high purity and sufficiently low toxicity to render them suitable for administration to the human or lower animal being treated. Such carrier preferably comprises from about 95% to about 99.99%, more preferably from about 98% to about 99.99%, more preferably still from about 98.5% to about 99.9%, more preferably still from about 99% to about 99.5% of the composition.

Topical Carriers

The topical compositions of the subject invention may be made into a wide variety of product types. These include, for example, lotions, creams, beach oils, gels, sticks, sprays, ointments, pastes, mousses and cosmetics. These product types may comprise either of two basic types of carrier systems, solutions and emulsions.

The topical compositions of the subject invention formulated as solutions typically include a pharmaceutically-acceptable aqueous or organic solvent. Preferred solvents, in addition to being capable of having dispersed or dissolved therein the active compound, also possesses acceptable safety (e.g., irritation and sensitization characteristics), as well as good aesthetic properties (e.g., does not feel greasy or tacky). Water is a typical aqueous solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanediol, and mixtures thereof. Preferred solutions of the subject invention comprise from about 0.01% to about 5%, more preferably from about 0.01% to about 2%, more preferably from about 0.1% to about 1.5%, more preferably from about 0.5% to about 1% of the active compound, and from about 95% to about 99.99%, more preferably from about 98% to about 99.99%, more preferably from about 98.5% to about 99.9%, more preferably from about 99% to about 99.5% of an acceptable organic solvent.

If the topical compositions of the subject invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972), incorporated herein by reference.

Topical compositions of the subject invention may be formulated as a solution comprising an emollient. An example of a composition formulated in this way would be a beach oil product. Such compositions typically comprise from about 0.01% to about 5%, preferably from about 0.01% to about 2%, more preferably from about 0.1% to about 1.5%, more preferably from about 0.5% to about 1% of the active compound and from about 1% to about 50%, preferably from about 5% to about 20% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 0.1% to about 5%, preferably from about 0.1% to about 2%, more preferably from about 0.5% to about 1.5%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the subject invention would comprise from about 0.1% to about 5%, preferably from about 0.1% to about 2%, more preferably from about 0.5% to about 1.5%, of the active compound;

from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Sagarin, *Cosmetics, Science and Technology*, 2nd Edition, Vol. 1, pp. 72–73 (1972), incorporated herein by reference.

If the carrier is formulated as an emulsion, from about 1% to about 10%, preferably from about 2% to about 5%, of the carrier system comprises an emulsifier. Emulsifiers may be nonionic, anionic or cationic.

Lotions and creams can be formulated as emulsions as well as solutions. Typically such lotions comprise from about 0.1% to about 5%, preferably from about 0.1% to about 2%, more preferably from about 0.5% to about 1.5%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.1% to about 5%, preferably from about 0.1% to about 2%, more preferably from about 0.5% to about 1.5%, of the active compound; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the topical compositions of the subject invention are formulated as a gel or a cosmetic stick, a suitable amount of a thickening agent is added to a cream or lotion formulation.

The topical compositions of the subject invention may also be formulated as makeup products such as foundations, or lipsticks.

The topical compositions of the subject invention may comprise, in addition to the aforementioned components, a wide variety of additional oil-soluble materials and/or water-soluble materials conventionally used in topical compositions, at their art-established levels.

Various water-soluble materials may also be subject in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

Compositions of the subject invention can be tested using either of the following test methods to determine effective dosage levels of the active compound.

Test Method—Guinea Pig SPF Test

The guinea pig is used as a model for determination of sun protection factor (SPF) values of topical protective agents; see, e.g., Leroy, D. & P. Deschamps, "Sunscreen Seawater Resistance: Comparison of Human and Guinea-pig Test Models", *Photodermatol.*, Vol. 2 (1985), pp. 38–40; and Bissett, D. L., J. F. McBride, D. P. Hannon, & L. F. Patrick, "Time-dependent Decrease in Sunscreen Protection Against Chronic Photodamage in UVB-irradiated Hairless Mouse Skin", *J. Photochem. Photobiol. B: Biol.*, Vol. 9 (1991), pp. 323–334; and "Sunscreen Drug Products for Over-the-counter Human Drugs", *Federal Register* (Food and Drug Administration), Vol. 43 (1978) p. 38259; all of which are incorporated herein by reference. This animal develops an erythemal response to UV radiation which is very similar to the human response, and photoprotective agent SPF values are similar in the two species.

Materials and Methods

Animals—Male Hartley strain guinea pigs are obtained from Charles River Laboratories, Portage, Mich. The guinea pigs weigh approximately 300 g at the start of experimental work. All animals are housed in indivudual cages in a room with controlled temperature and humidity and with a 12-hour light/darkness cycle. They are given a standard Purina Chow diet and water ad libitum.

UV Radiation Source and Radiometer—A model 81172 Oriel Corp. (Stratford, Conn.) solar simulator equipped with a 1000-watt zenon arc ozone-free lamp is used. Schott Glass Technologies, Inc. (Duryea, Pa.) filters (a 3-mm WG-305 (to remove UVC) and a 1-mm UG-5 filter (to remove visible light)) are inserted in the light path just past the simulator output port to simulate the solar UV spectrum. Total UVB or UVA output is determined with an International Light (Newburyport, Mass.) model IL1350 radiometer equipped with SED 240 (UVB) and SED 015 (UVA) sensors. Spectral scans are recorded on a model 4950 strip chart recorder (Bausch & Lomb, Austin, Tx.) using an International Light double monochrometer spectro-radiometer system (model IL 700A/760/791 ).

Guinea Pig SPF Measurements—The dorsal skin of guinea pigs is shaved with electric clippers and then depilated with Neet® Lotion Hair Remover (Whitehall Laboratories, New York, N.Y.). The skin is rinsed under warm tap water and dried with a towel. Sixteen hours later, the dorsal skin is treated with 2 mg/cm$^2$ of test material solution.

The animals (n=5 per treatment group) are then wrapped with 3-inch wide tape (Elastoplast®, Beiersdorf Inc., Norwalk, Conn.) containing four 2-cm diameter exposure windows (two windows on each side of the spinal area). The adhesive side of the tape covering the dorsal skin area is coated with black construction paper to prevent reddening of the skin from adherence of the tape to that skin region. The time between topical treatment and irradiation with UV-light is approximately 15 minutes.

Animals are restrained with a neck clip and exposed individually. Each animal is positioned with its dorsal skin surface 18 inches below the filter set of the solar simulator. The irradiance at this distance is approximately 0.45 mW/cm$^2$ UVB and 10.2 mW/cm$^2$ UVA. Irradiation times of the four exposure windows on each animal are set to bracket the suspected SPF of the material being tested. Exposure windows are covered with opaque tape at the end of each time point. At the completion of all irradiations, all tape is removed from the animals.

Erythema is scored (0–3 grading scale, with half grade increments) 24 hours later, using non-exposed adjacent skin on each animal as no UV control (score = 0). A grade of 1.0 (detectable redness over the entire exposure area) is considered 1 MED. SPF is then calculated from the ratio: (UV dose to achieve 1 MED with test material)/(UV dose to achieve 1 MED without test material).

The compositions of the subject invention can comprise other photoprotectively active compounds such as sunscreens, sunblocks, anti-inflammatories, antioxidants or radical scavengers.

Combination Actives

A. Sunscreens and Sunblocks

Optimum protection against sun damage can be obtained by using a combination of the active compounds of the subject invention together with sunscreens or sunblocks. Useful sunblocks include, for example, zinc oxide and titanium dioxide.

If the photoprotecting capability of the active compound is primarily active against UVB radiation, a combination of the active compound with a UVA sunscreen would be most desirable. Conversely, if the active compound is primarily active against UVA radiation, a combination of the active compound with a UVB sunscreen would be most desirable. Additional UVA and/or UVB protection may also be included in such compositions. The inclusion of sunscreens in compositions of the subject invention at low levels will not significantly reduce the tanning response of the user but will enhance immediate protection against acute UV damage.

A wide variety of conventional sunscreening agents are suitable for use in combination with the active compounds. Sagarin, et al., Vol. 1, at Chapter VII, pages 293 et seq., of *Cosmetics Science and Technology*, incorporated herein by reference, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, octyl, menthyl, glyceryl, and dipropyleneglycol esters); Cinnamic acid derivatives (menthyl and benzyl esters, a-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric acid; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; t-Butylmethoxydibenzoylmethane; Etocrylene; and 4-isopropyldibenzoylmethane.

Of these, 2-ethylhexyl-p-methoxycinnamate, 4,4'-t-butyl-methoxydibenzoylmethane, 2-hydroxy-4-methoxybenzophenone, octyldimethylp-aminobenzoic acid, digalloyltrioleate, 2,2-dihydroxy-4-methoxybenzophenone, ethyl-4-(bis(hydroxypropyl) )aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethylamino-benzoate, 2-phenylbenzimidazole- 5-sulfonic acid, 2-(p-dimethylaminophenyl)-5-sulfonicbenzoxazoic acid, 7-diethylamino-4-methylcoumarin and mixtures of these compounds, are particularly useful.

Preferred sunscreens useful in the compositions of the subject invention are 2-ethylhexyl-p-methoxycinnamate, butylmethoxydibenzoylmethane, 2-hydroxy-4-methoxybenzophenone, octyldimethyl p-aminobenzoic acid and mixtures thereof.

A safe and photoprotectively effective amount of sunscreen may be used in the compositions of the subject invention. The sunscreening agent must be compatible with the active compound. Generally the composition may comprise from about 1% to about 20%, preferably from about 2% to about 10%, of a sunscreening agent. Exact amounts will vary depending upon the sunscreen chosen and the desired Sun Protection Factor (SPF). Because of the photoprotecting capability of the active compound against erythema, the combination provides an SPF greater than that of the sunscreen alone.

Also particularly useful in the subject invention are sunscreens such as those disclosed in U.S. Pat. No. 4,937,370 issued to Sabatelli on Jun. 26, 1990, and in U.S. Pat. No. 4,999,186 issued to Sabatelli and Spirnak on Mar. 12, 1991, both incorporated herein by reference. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range.

The compositions of the subject invention, with or without sunscreens, may also be formulated as shampoos, conditioners, mousses or other hair care products. It is known that UV radiation damages hair and the photoprotecting agents of the subject invention may minimize such damage. Furthermore such formulations will provide a means for applying the photoprotecting agents of the subject invention onto the scalp, which is also susceptible to UV damage. Any compatible art-recognized hair care formulations can be used with the active compound added at a level of from about 1% to about 5% or from about 1% to about 2%. If desired, a sunscreen may also be included at from about 1% to about 5%.

An agent may also be added to any of the compositions of the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred photoprotection composition of the subject invention, an anti-inflammatory agent is included as an active along with the active compound. The anti-inflammatory agent protects strongly in the UVA radiation range (though it also provides some UVB protection as well). The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989; and U.S. Pat. No. 4,847,069, Bissett and Chatterjee, issued Jul. 11, 1989, both incorporated herein by reference. )

A safe and effective amount of an anti-inflammatory agent may be added to the compositions of the subject invention, generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

A preferred composition of the subject invention comprises each of an active compound, a sunscreen, and an anti-inflammatory agent together for photoprotection in the amounts disclosed for each individually hereinabove.

Method For Preventinfi Deleterious Effects Caused By UV Exposure

The subject invention further relates to a method for protecting the skin of humans and lower animals from the deleterious effects of radiation, particularly UV radiation, and/or other causes of metal-catalyzed free radical production in the skin tissue. Such protection by the active compound extends to damage resulting from acute UV exposure, e.g. erythema. It also extends to protection from damage resulting from chronic UV exposure, e.g. photoaging. Such protection also extends to damage resulting from sources of radiation other than the sun; non-limiting examples include ultraviolet lights (e.g., tanning lights), x-rays, lasers, etc.

Such a method comprises applying to the skin of the human or lower animal a safe and effective amount of the active compounds disclosed hereinabove to be useful in the subject invention. This may be accomplished by using a composition comprising the active compound as disclosed hereinabove. The active compounds involved in each of the following methods may be simply spread over the skin, or rubbed into the skin to enhance penetration of the active compound. The active compounds are preferably applied in conjunction with UV exposure, i.e., prior to, during, or after UV exposure. More specifically, the active compounds are preferably applied from several hours, preferably up to 4 hours, prior to UV exposure, to up to 30 minutes after UV exposure, or anytime in between.

For protection against acute damage from UV radiation, topical application of the active compounds prior to exposure of the skin to UV radiation is preferred.

For protection against chronic damage from UV radiation, topical application of the active compounds is preferably done on a chronic basis. The active compounds are preferably topically applied to the skin about daily, preferably prior to substantial exposure of the skin to UV radiation. Such application preferably occurs from at least about once to about 5 times daily, more preferably about 2 times daily, but for particularly effective compositions preferably once daily. Such application preferably occurs over long periods of time, preferably for more than one month, more preferably for more than six months, more preferably still for more than one year, 5 years, 10 years or more.

Typically a safe and photoprotectively effective amount of an active compound is from about 0.001 mg to about 2.0 mg, preferably from about 0.001 mg to about 1.0 mg, more preferably from about 0.01 mg to about 0.5 mg, more preferably from about 0.05 mg to about 0.1 mg of the active compound per $cm^2$ skin.

A preferred method of the subject invention for preventing deleterious effects caused by UV exposure involves applying both a safe and photoprotectively effective amount of an active compound and a safe and photoprotectively effective amount of one or more of an additional sunscreening agent, and/or an anti-inflammatory agent, to the skin simultaneously. By "simultaneous application" or "simultaneously" is meant applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.01 mg to about 1.0 mg. preferably from about 0.05 mg to about 0.5 mg, per $cm^2$ of skin. The amount of anti-inflammatory agent is generally from about 0.005 mg to about 0.5 mg, preferably from about 0.01 mg to about 0.1 mg.

The following examples further describe and demonstrate the preferred embodiments within the scope of the subject invention. The examples are given solely for the purpose of illustration, and are not to be construed as limitations of the subject invention since many variations thereof are possible without departing from its spirit and scope.

EXAMPLE 15

A moisturizing lotion is prepared by combining the following components utilizing conventional mixing techniques.

| Component | Percent by Weight of Composition |
| --- | --- |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 3.00 |
| $C_{12}$–$C_{15}$ Alcohol Benzoate (Finsolv TN - commercially available from Finetex, Inc.) | 3.00 |
| 1,3-Di(n-butyl)-violuric acid | 1.00 |
| Dimethicone | 0.30 |
| Imidazolidinyl Urea | 0.40 |
| Water | q.s. |

This lotion may be topically applied to inhibit damage caused by radiation, particularly acute or chronic UV exposure. Use of an amount of lotion sufficient to deposit about 0.5 mg/$cm^2$ of 1,3-di(n-butyl)-violuric acid to the skin is appropriate.

EXAMPLES 16 & 17

Skin lotions are prepared by combining the following components utilizing conventional mixing techniques.

| | Percent by Weight of Composition | |
| --- | --- | --- |
| Component | Example 16 | Example 17 |
| 4-N,N-(2-Ethylhexyl)methylamino-benzoic Acid Ester of 4-(2-Hydroxyethoxy)-dibenzoylmethane | 5.00 | — |
| Dioctyl Maleate | 8.00 | 2.00 |
| $C_{12}$–$C_{15}$ Alcohol Benzoate (Finsolv TN-commercially available from Finetex, Inc.) | 8.00 | 2.00 |
| Glycerin | 3.50 | 3.50 |
| Ethylene Acrylate Copolymer | 3.80 | 3.80 |
| 1,3-Di(ethoxyethyl)-violuric acid | 0.5 | 2.00 |
| Cetyl Alcohol | 1.75 | 1.75 |
| Polyoxyethylene Stearyl Alcohol (commercially available in the Brij series from ICI Americas, Inc.) | 1.75 | 1.75 |
| Stearic Acid | 1.25 | 1.25 |

-continued

| Component | Percent by Weight of Composition | |
|---|---|---|
| | Example 16 | Example 17 |
| Glyceryl Stearate | 1.13 | 1.13 |
| Alkyl Parabens | 0.90 | 0.90 |
| Titanium Dioxide | 0.40 | — |
| Dimethicone | 0.30 | 0.30 |
| Carbomer viscosity control agents (commercially available as Acritamer from R.I.T.A. Corp.) | 0.23 | 0.23 |
| Potassium Hydroxide | 0.15 | 0.15 |
| Tetrasodium EDTA | 0.10 | 0.10 |
| Water | q.s. | q.s. |

These lotions are useful for topical application to inhibit damage caused by radiation, particularly acute or chronic UV exposure. Use of an amount of lotion sufficient to deposit about 0.5 mg/cm$^2$ of 1,3-di(ethoxyethyl)-violuric acid to the skin prior to radiation exposure is appropriate.

EXAMPLES 18 & 19

Suntan creams are prepared by combining the following components utilizing conventional mixing techniques.

| Component | Percent by Weight of Composition | |
|---|---|---|
| | Example 18 | Example 19 |
| Mineral Oil | 20.00 | 20.00 |
| Octyl Palmitate | 10.00 | 10.00 |
| Glyceryl Isostearate | 4.00 | 4.00 |
| Octyl Methoxycinnamate | 7.50 | — |
| Oxybenzone | 3.00 | — |
| Polyethylene (AC-617-A, AC-6-A available from Allied Chemical) | 2.00 | 2.00 |
| Dowicil 200 (Quaternum/s) | .20 | .20 |
| Alkyl parabens | 0.30 | 0.30 |
| Glycerin | 2.00 | 2.00 |
| 1,3-Di(carbethoxymethyl)-violuric acid | 1.00 | 0.5 |
| Ibuprofen | 1.00 | — |
| Water | q.s. | q.s. |

These creams are useful for topical application to inhibit damage caused by radiation, particularly acute or chronic UV exposure. Use of an amount of cream sufficient to deposit about 0.5 mg/cm$^2$ and 1.2 mg/cm$^2$ of 1,3-di(carbethoxymethyl)-violuric acid to the skin for Examples 18 and 19, respectively, is appropriate.

EXAMPLE 20

A suntan stick is prepared by combining the following components utilizing conventional mixing techniques.

| Component | Percent by Weight of Composition |
|---|---|
| Candelilla Wax | 20.00 |
| Ozokerite Wax | 20.00 |
| Petrolatum | 20.00 |
| Lanolin | q.s. |
| Mineral Oil | 14.85 |
| Octyl Dimethyl PABA | 4.00 |
| Benzophenone-3 | 1.00 |
| BHA (preservative: butylated hydroxy | 0.05 |

-continued

| Component | Percent by Weight of Composition |
|---|---|
| anisole) | |
| Propylparaben | 0.10 |
| 1,3-Diethyl-violuric acid | 1.00 |

This stick is useful for topical application, for example to the lips, to inhibit damage caused by radiation, particularly acute or chronic UV exposure. Use of an amount of stick sufficient to deposit about 1.0 mg/cm$^2$ of 1,3-Diethyl-violuric acid to the lips prior to UV exposure is appropriate.

EXAMPLE 21

A suntan cream is prepared by combining the following components utilizing conventional mixing techniques.

| Component | Percent by Weight of Composition |
|---|---|
| Tetrasodium EDTA | 0.05 |
| Germall 1/5 | 0.30 |
| Alkylparabens | 0.30 |
| Carbopol (polyacrylic acid polymer-commercially available from B. F. Goodrich Chemical) | 0.20 |
| Glycerin | 2.00 |
| Laureth-23 (polyethylene glycol ether of lauryl alcohol) | 1.00 |
| Sorbitan Stearate | 1.50 |
| Octyl Dimethyl PABA | 3.00 |
| Dimethicone | 2.00 |
| Stearyl Alcohol | 3.00 |
| Cetyl alcohol | 3.00 |
| Triethanolamine | 0.20 |
| 1,3-Di-tert-butylvioluric acid | 1.00 |
| Water | q.s. |

This cream is useful for topical application to inhibit damage caused by radiation, particularly acute or chronic UV exposure. Use of an amount of cream sufficient to deposit about 0.2 mg/cm$^2$ of 1,3-di-tert-butylvioluric acid to the skin prior to UV exposure is appropriate.

EXAMPLE 22

A suntan aqueous face gel is prepared by combining the following components utilizing conventional mixing techniques.

| Component | Percent by Weight Of Composition |
|---|---|
| Water | q.s. |
| Aloe | 38.00 |
| Carbopol | 1.00 |
| Glycerin | 3.00 |
| Methylparaben | 0.20 |
| Triethanolamine | 0.90 |
| 2-Phenylbenzimidazole-5-sulfonic acid | 2.00 |
| Arlosolv 200 (Isoeath 20) | 5.00 |
| Dimethyl Isorbine | 5.00 |
| 1,3-Diphenylvioluric acid | 1.00 |
| Color and Fragrance | q.s. |

This aqueous gel is useful for application to the face to inhibit damage caused by radiation, particularly acute or chronic UV exposure. Use of an amount of gel to deposit about 0.5 mg/cm² of 1,3-diphenylvioluric acid to the face prior to UV exposure is appropriate.

EXAMPLE 23

A suntan gel is prepared by combining the following components utilizing conventional mixing techniques.

| Component | Percent by Weight of Composition |
|---|---|
| Ozokerite Wax | 10.00 |
| Paraffin | 10.00 |
| Petrolatum | 10.00 |
| Isopropyl Myristate | 5.00 |
| Octyl Methoxycinnamate | 2.50 |
| Propylparaben | 0.10 |
| BHA | 0.05 |
| Violuric acid | 0.50 |
| Naproxen | 2.00 |
| Mineral Oil | q.s. |
| Fragrance and Color | 0.5 |

This suntan gel is useful for topical application to inhibit damage caused by radiation, particularly acute or chronic UV exposure. Use of an amount of gel to deposit about 0.5 mg/cm² of violuric acid to the skin is appropriate.

EXAMPLE 24

A suntan oil is prepared by combining the following components utilizing conventional mixing techniques.

| Component | Percent by Weight of Composition |
|---|---|
| Sesame Oil | 5.0 |
| Cyclomethicone | 20.0 |
| Isopropyl Myristate | 5.0 |
| BHA | 0.05 |
| Sorbitan Oleate | 1.0 |
| Octyl Methoxycinnamate | 1.5 |
| Propylparaben | 0.7 |
| 1,3-Di(n-butyl)-violuric acid | 2.0 |
| Mineral Oil | q.s. |

This suntan oil is useful for topical application to inhibit damage caused by radiation, particularly acute or chronic UV exposure. Use of an amount of oil sufficient to deposit about 0.8 mg/cm² of 1,3-di(n-butyl)-violuric acid to the skin prior to UV exposure is appropriate.

EXAMPLE 25

A moisturizing oil-in-water-in-silicone sunscreen emulsion lotion is formed from the following ingredients.

| Ingredient | Percent by Weight of Composition |
|---|---|
| Aqueous Phase: | |
| Water | q.s. |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodium alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |
| Color & Fragrance: | |
| FD&C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic $C_{11}$–$C_{15}$ fatty alcohol, av.3 moles EO) | 2.00 |
| Octyl Methoxycinnamate | 7.00 |
| Benzophenone-3 | 0.50 |
| Naproxen | 2.00 |
| 1,3-Di(1-carboxypropyl)-violuric acid | 0.5 |
| $C_{12}$–$C_{15}$ Alcohol Benzoate | 2.85 |

In a suitably sized vessel equipped with a suitable mechanical stirrer (Tekmar Model RW-20 stirring motor, manufactured by IKA-WERK, Germany), the water, pantethine, methylparaben, glycerine and sulfonate emulsifier are heated to about 72°–75° C. and mixed. Stirring is increased until a vortex forms in the aqueous solution. The thickener, Carbomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen, and 1,3-di(1-carboxypropyl)-violuric acid are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°–50° C. and the colorant and odorant oil are added followed by cooling to room temperature (about 25° C.) with continued moderate agitation.

The four silicone fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturizing lotion is useful for topical application to inhibit damage caused by radiation, particularly acute or chronic UV exposure. Use of an amount of lotion sufficient to deposit about 0.5 mg/cm$^2$ of 1,3-di(1-carboxypropyl)-violuric acid to the skin is appropriate. This lotion may also be applied several times daily, e.g., 2 or 3 times daily, for extended periods of time, i.e., greater than one week, in amounts sufficient to deposit about 0.5 mg/cm$^2$ of 1,3-di(1-carboxypropyl)-violuric acid to the skin to inhibit damage caused by chronic UV exposure.

EXAMPLE 26

A skin conditioning toilet bar is prepared from the following ingredients.

| Component | Percent by Weight of Composition |
| --- | --- |
| Tallow/Coconut Soap (50/50) | q.s. |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| 5,5-Dimethyl-1,3-cyclohexanedione-2-oxime | 1.00 |
| Perfume | 1.40 |
| NaCl | 1.04 |
| Na$_2$SO$_4$ | 0.34 |
| Na$_4$EDTA | 0.06 |
| TiO$_2$ | 0.20 |
| Jaguar C15 (guar hydroxypropyltrimonium chloride) | 1.00 |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°–200° F. (65°–94° C.). About 10.0 parts of the hydrated polymer JAGUAR C-15 are mixed in. The 5,5-dimethyl-1,3-cyclohexanedione-2-oxime is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 pad TiO$_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°–105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

The use of this toilet bar for cleansing provides a useful means for deposition of 5,5-dimethyl-1,3-cyclohexanedione-2-oxime to the skin to inhibit damage caused by radiation, particularly acute or chronic UV exposure. Use of the toilet bar such that about 0.05 mg/cm$^2$ of 5,5-dimethyl-1,3-cyclohexanedione-2-oxime is deposited on the skin is appropriate.

EXAMPLE 27

A facial cleanser (lathering mousse composition) is prepared from the following ingredients.

| | Percent by Weight of Composition |
| --- | --- |
| Emulsion Concentrate (A) | |
| DRO Water[1] | q.s. |
| 2-Hydroxypropyglyceryl Ether | 15.00 |
| Sodium Glyceryl Ether Sulfonate (90% Coconut/10 Tallow)-50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| 2,2-Dimethyl-1,3-dioxane-4,6-dione-5-oxime | 2.00 |
| Jaguar C14-S (guar hydroxypropyltrimonium chloride) | 0.25 |
| Perfume | 0.20 |
| FD&C Red Dye #4 | 0.20 |
| Lauryl Alcohol | 0.20 |
| Alkyl Parabens | 0.30 |
| Germall 115 (Imidazolidinyl urea) | 0.10 |
| Na$_4$EDTA | 0.10 |
| [1]Water purified by double reverse osmosis | |
| A-46 Propellant (Isobutane-Propane) (B) | |

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and 2,2-dimethyl-1,3-dioxane-4,6-dione-5-oxime. The mixture is then cooled to 135°–140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of 2,2-dimethyl-1,3-dioxane- 4,6-dione-5-oxime to the skin to inhibit damage caused by radiation, particularly acute or chronic UV exposure. Use of amount of facial cleanser sufficient to deposit about 0.05 mg/cm$^2$ of 2,2-dimethyl-1,3-dioxane-4,6-dione-5-oxime to the skin is appropriate.

EXAMPLE 28

A cream soap is prepared by combining the following ingredients as described below.

| Component | Percent by Weight of Composition |
| --- | --- |
| Sodium Lauroyl Glutamate (Acylglutamate LS-11) (28) | 23.00 |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| 5,5-Dimethyl-1,3-cyclohexanedione-2-oxime | 1.00 |
| Tocopherol Sorbate | 5.00 |
| Flufenamic Acid | 2.00 |
| 2-Ethylhexyl Methoxycinnamate | 3.00 |
| Water | q.s. |
| Glycerin | 10.00 |
| Fragrance and Preservative | 0.5 |

The sodium glutamate, sodium hydrogenated tallow glutamate and cocoyl glutamate, polyethylene glycol, polyethylene glycol monostearate, polyoxyethylene sorbitan monostearate, 5,5-dimethyl-1,3-cyclohexanedione-2-oxime, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of 5,5-dimethyl-1,3-cyclohexanedione-2-oxime to the skin to inhibit damage caused by radiation, particularly acute or chronic UV exposure. Use of an amount of cream soap sufficient to deposit about 0.05 mg/cm$^2$ of 5,5-dimethyl-1,3-cyclohexanedione-2-oxime to the skin is appropriate.

EXAMPLE 29

A shampoo composition is made by combining the following components.

| Component | Percent by Weight of Composition |
| --- | --- |
| Ammonium Lauryl Sulfate | 12.0 |
| Ammonium Xylene Sulfonate | 2.2 |
| Ammonium Laureth Sulfate | 4.0 |
| NaCl | 0.5 |
| 2,2-Dimethyl-1,3-dioxane-A,6-dione-5-oxime | 2.0 |
| Octyl Dimethyl PABA | 7.0 |
| Perfume and Minor Ingredients | 1.2 |
| Water | q.s. |

The ammonium lauryl sulfate, ammonium laureth sulfate, and ammonium xylene sulfonate are first mixed together. The 2,2-dimethyl-1,3-dioxane-4,6-dione- 5-oxime and octyl dimethyl PABA and perfume and minor ingredients are added and the resulting mixture is agitated in a Teckmar® Mill set at 70 for 2 minutes at 70° C.

The resulting shampoo composition is added to hair which has been wetted with water, worked through the hair then rinsed out. This allows for deposition of 2,2-dimethyl-1,3-dioxane-4,6-dione-5-oxime and octyl dimethyl PABA to the scalp to inhibit damage caused by acute or chronic UV exposure. Use of an amount of shampoo sufficient to deposit about 0.05 mg/cm$^2$ of 2,2-dimethyl- 1,3-dioxane-4,6-dione-5-oxime to the scalp is appropriate.

EXAMPLES 30 & 31

Simple solutions are made by combining the following components:

| | Percent by Weight of Composition | |
| --- | --- | --- |
| Component | Example 30 | Example 31 |
| Propylene glycol | 27.6 | 28.5 |
| Water | 21.3 | 22.0 |
| Violuric acid | 1.0 | 2.0 |
| Ethanol, absolute | q.s. | q.s. |

The propylene glycol, ethanol and water are first mixed together in proportions of 25:55:20 v:v:v, respectively. This solution is then combined with violuric acid in proportions of 95:5 w:w for Example 30 and 98:2 w:w for Example 31 to produce the final solutions. Topical application of these solutions in an amount sufficient to deposit about 0.2 mg/cm$^2$ for Example 30 and 0.07 mg/cm$^2$ for Example 31 of violuric acid to the skin inhibits damage caused by radiation, particularly acute or chronic UV exposure.

While particular embodiments of the subject invention have been described, it will be obvious to those skilled in the art that various changes and modifications of the subject invention can be made without departing from the spirit and the scope of the invention. It is intended to cover, in the appended claims, all such modifications that are within the scope of this invention.

EXAMPLE 32

| | Acne Gal. | Preparation |
| --- | --- | --- |
| Di Water | q.s. | |
| Ethanol | 4.0 | |
| Salcare qs | 4.0 | |
| Salicaylic Acid | 2.0 | |
| Active | 1.0 | |
| Triethanalamine | 0.2 | |

EXAMPLE 33

| | Acne Moisturizer |
| --- | --- |
| Di Water | q.s |
| Glycerine | 3.00 |
| Na$_2$EDTA | 0.05 |
| Fluid AP | 8.00 |
| Cetyl Alcohol | 1.00 |
| Stearyl Alcohol | 1.00 |

-continued

| Acne Moisturizer | |
|---|---|
| Salicylic Acid | 2.00 |
| Saline SCQS | 2.00 |

What is claimed is:

1. A photoprotective topical composition comprising:
(a) from about 0.01% to about 5% of an active compound having the structure selected from the group consisting of:

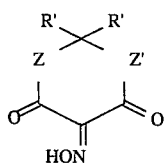

wherein each R' is independently selected from the group consisting of hydrogen, substituted or unsubstituted alkoxy, and substituted or unsubstituted alkyl; Z and Z' are independently selected from the group consisting of NH, O and $CH_2$ such that when either Z' or Z is NH, the other is not O; or a pharmaceutically acceptable salt of any of the aforementioned compounds; and (b) a pharmaceutically-acceptable topical carrier comprising one or more cosmetic adjuvants.

2. The composition of claim 1 wherein each R' is independently selected from the group consisting of hydrogen; $C_1$–$C_{10}$ straight and branched chain alkyl, unsubstituted or substituted with halogen, hydroxy, alkoxy, carboxy, carboxy esters, oxo, thiol, alkylthio, alkyldithio, amino, alkylamino, dialkylamino, amide, alkylamide, dialkylamide, and alkylsilyl; and Z and Z' are each independently selected from the group consisting of O and $CH_2$.

3. The composition of claim 2 wherein each R' is independently selected from the group consisting of hydrogen, $C_3$–$C_6$ branched chain alkyl, $C_1$–$C_6$ straight chain substituted alkyl, and $C_1$–$C_4$ straight chain unsubstituted alkyl.

4. The composition of claim 3 wherein both R' are the same.

5. The composition of claim 4 wherein R' is methyl.

6. The composition of claim 5 wherein Z and Z' are O.

7. The composition of claim 1 wherein the pharmaceutically acceptable topical carrier comprises from about 0.5% to about 2% of the compound and from about 5% to about 20% of an emollient.

8. The composition of claim 1 wherein the pharmaceutically acceptable topical carrier also comprises an active agent selected from the group consisting of a sunscreen, a sunblock, and an anti-inflammatory.

9. The composition of claim 1 wherein the active compound is complexed with a metal ion.

10. The composition of claim 1 wherein the compound is complexed with a metal ion, wherein the metal ion is substantially complexed and is selected from the group consisting of sodium, aluminum, zinc, lithium, gallium and scandium.

11. A method for protecting the skin of a human or lower animal from radiation by topically administering to the skin a safe and effective amount of the composition of claim 1.

12. A method for preventing premature aging of skin of a human or lower animal by administering to the skin a composition of claim 1 so as to deliver from about 0.001 mg to about 2.0 mg of the active compound per $cm^2$ skin, about once or more daily for about one month or more.

* * * * *